(12) United States Patent
Nita

(10) Patent No.: US 8,246,643 B2
(45) Date of Patent: Aug. 21, 2012

(54) ULTRASOUND CATHETER HAVING IMPROVED DISTAL END

(75) Inventor: Henry Nita, Redwood Shores, CA (US)

(73) Assignee: Flowcardia, Inc., Sunnyvale, CA (US)

( * ) Notice: Subject to any disclaimer, the term of this patent is extended or adjusted under 35 U.S.C. 154(b) by 390 days.

(21) Appl. No.: 12/218,827

(22) Filed: Jul. 18, 2008

(65) Prior Publication Data
US 2008/0287804 A1 Nov. 20, 2008

Related U.S. Application Data

(63) Continuation-in-part of application No. 12/004,984, filed on Dec. 21, 2007, which is a continuation-in-part of application No. 11/594,663, filed on Nov. 7, 2006, now Pat. No. 8,133,236.

(51) Int. Cl.
*A61B 17/32* (2006.01)

(52) U.S. Cl. ........................................ 606/169; 606/171

(58) Field of Classification Search .................. 606/128, 606/159, 169, 171; 604/22; 601/2; 600/466, 600/467, 436, 529, 468, 4, 461, 104
See application file for complete search history.

(56) References Cited

U.S. PATENT DOCUMENTS

| | | |
|---|---|---|
| 3,433,226 A | 3/1969 | Boyd |
| 3,565,062 A | 2/1971 | Kuris |
| 3,631,848 A | 1/1972 | Muller |
| 3,719,737 A | 3/1973 | Vaillancourt et al. |
| 3,823,717 A | 7/1974 | Pohlman et al. |
| 3,896,811 A | 7/1975 | Storz |
| 4,016,882 A | 4/1977 | Broadwin et al. |
| 4,033,331 A | 7/1977 | Guss et al. |
| 4,136,700 A | 1/1979 | Broadwin et al. |
| 4,337,090 A | 6/1982 | Harrison |
| 4,368,410 A | 1/1983 | Hance |
| 4,417,578 A | 11/1983 | Banko |
| 4,425,115 A | 1/1984 | Wuchinich |

(Continued)

FOREIGN PATENT DOCUMENTS

DE 2256127 5/1974

(Continued)

OTHER PUBLICATIONS

Siegel, et al., "In Vivo Ultrasound Arterial Recanalization of Atherosclerotic Total Occlusions", Journal of the American College of Cardiology, Feb. 1990, vol. 15, No. 2, pp. 345-351.

(Continued)

*Primary Examiner* — Ryan Severson
*Assistant Examiner* — Tin Nguyen
(74) *Attorney, Agent, or Firm* — Knobbe, Martens, Olson & Bear LLP

(57) ABSTRACT

An ultrasound catheter has an elongate flexible catheter body having a lumen extending longitudinally therethrough, and an ultrasound transmission member extending longitudinally through the lumen of the catheter body. The ultrasound transmission member has a proximal end that is coupled to a separate ultrasound generating device, and a distal tip that is attached to the distal end of the ultrasound transmission member and which is located at the distal end of the catheter body. The distal tip has at least one dimensional step. The ultrasound transmission member is directly attached to the catheter body and/or to a guidewire tube, either directly or via an attachment device. The catheter has an additional radiopaque marker positioned on the distal end the catheter.

23 Claims, 11 Drawing Sheets

U.S. PATENT DOCUMENTS

| | | | |
|---|---|---|---|
| 4,486,680 A | 12/1984 | Bonnet et al. | |
| 4,505,767 A | 3/1985 | Quin | |
| 4,565,589 A | 1/1986 | Harrison | |
| 4,572,184 A | 2/1986 | Stohl et al. | |
| 4,664,112 A | 5/1987 | Kensey et al. | |
| 4,665,906 A | 5/1987 | Jervis | |
| 4,679,558 A | 7/1987 | Kensey et al. | |
| 4,700,705 A | 10/1987 | Kensey et al. | |
| 4,721,117 A | 1/1988 | Mar et al. | |
| 4,750,902 A | 6/1988 | Wuchinich et al. | |
| 4,808,153 A | 2/1989 | Parisi | |
| 4,811,743 A | 3/1989 | Stevens | |
| 4,827,911 A | 5/1989 | Broadwin et al. | |
| 4,838,853 A | 6/1989 | Parisi | |
| 4,854,325 A | 8/1989 | Stevens | |
| 4,870,953 A | 10/1989 | DonMicheal et al. | |
| 4,886,060 A | 12/1989 | Wiksell | |
| 4,920,954 A | 5/1990 | Alliger | |
| 4,923,462 A | 5/1990 | Stevens | |
| 4,924,863 A | 5/1990 | Sterzer | |
| 4,931,047 A | 6/1990 | Broadwin et al. | |
| 4,936,281 A | 6/1990 | Stasz | |
| 4,936,845 A | 6/1990 | Stevens | |
| 5,000,185 A | 3/1991 | Yock | |
| 5,015,227 A | 5/1991 | Broadwin et al. | |
| 5,026,384 A | 6/1991 | Farr et al. | |
| 5,046,503 A | 9/1991 | Schneiderman | |
| 5,053,008 A | 10/1991 | Bajaj | |
| 5,058,570 A | 10/1991 | Idemoto et al. | |
| 5,076,276 A | 12/1991 | Sakurai et al. | |
| 5,091,205 A | 2/1992 | Fan | |
| 5,100,423 A | 3/1992 | Fearnot | |
| 5,114,414 A | 5/1992 | Buchbinder | |
| 5,116,350 A | 5/1992 | Stevens | |
| 5,127,917 A | 7/1992 | Niederhauser et al. | |
| 5,156,143 A | 10/1992 | Bocquet et al. | |
| 5,163,421 A | 11/1992 | Bernstein | |
| 5,180,363 A | 1/1993 | Idemoto et al. | |
| 5,195,955 A | 3/1993 | Don Michael | |
| 5,215,614 A | 6/1993 | Wijkamp et al. | |
| 5,221,255 A | 6/1993 | Mahurkar et al. | |
| 5,226,421 A | 7/1993 | Frisbie et al. | |
| 5,234,416 A | 8/1993 | Macaulay et al. | |
| 5,238,004 A | 8/1993 | Sahatjian et al. | |
| 5,242,385 A | 9/1993 | Strukel | |
| 5,243,997 A | 9/1993 | Uflacker et al. | |
| 5,248,296 A | 9/1993 | Alliger | |
| 5,255,669 A | 10/1993 | Kubota et al. | |
| 5,267,954 A | 12/1993 | Nita | |
| 5,269,291 A | 12/1993 | Carter | |
| 5,269,297 A | 12/1993 | Weng | |
| 5,269,793 A | 12/1993 | Simpson | |
| 5,287,858 A | 2/1994 | Hammerslag et al. | |
| 5,290,229 A | 3/1994 | Paskar | |
| 5,304,115 A | 4/1994 | Pflueger | |
| 5,304,131 A | 4/1994 | Paskar | |
| 5,312,328 A | 5/1994 | Nita et al. | |
| 5,324,255 A | 6/1994 | Passafaro et al. | |
| 5,324,260 A | 6/1994 | O'Neill et al. | |
| 5,325,860 A | 7/1994 | Seward et al. | |
| 5,326,342 A | 7/1994 | Pflueger et al. | |
| 5,341,818 A | 8/1994 | Abrams et al. | |
| 5,342,292 A * | 8/1994 | Nita et al. | 604/22 |
| 5,344,395 A | 9/1994 | Whalen et al. | |
| 5,346,502 A | 9/1994 | Estabrook et al. | |
| 5,362,309 A | 11/1994 | Carter | |
| 5,368,557 A | 11/1994 | Nita | |
| 5,368,558 A | 11/1994 | Nita | |
| 5,378,234 A | 1/1995 | Hammerslag et al. | |
| 5,380,274 A * | 1/1995 | Nita | 604/22 |
| 5,380,316 A | 1/1995 | Aita et al. | |
| 5,382,228 A | 1/1995 | Nita et al. | |
| 5,383,460 A | 1/1995 | Jang et al. | |
| 5,389,096 A | 2/1995 | Aita et al. | |
| 5,397,293 A | 3/1995 | Alliger | |
| 5,397,301 A * | 3/1995 | Pflueger et al. | 604/22 |
| 5,405,318 A | 4/1995 | Nita | |
| 5,409,483 A | 4/1995 | Campbell et al. | |
| 5,417,703 A | 5/1995 | Brown et al. | |
| 5,427,118 A | 6/1995 | Nita | |
| 5,431,168 A | 7/1995 | Webster, Jr. | |
| 5,431,663 A | 7/1995 | Carter | |
| 5,443,078 A | 8/1995 | Uflacker | |
| 5,447,509 A | 9/1995 | Mills et al. | |
| 5,449,369 A | 9/1995 | Imran | |
| 5,451,209 A | 9/1995 | Ainsworth et al. | |
| 5,465,733 A | 11/1995 | Hinohara et al. | |
| 5,480,379 A | 1/1996 | La Rosa | |
| 5,484,398 A | 1/1996 | Stoddard | |
| 5,487,757 A | 1/1996 | Truckai et al. | |
| 5,507,738 A | 4/1996 | Ciervo | |
| 5,516,043 A * | 5/1996 | Manna et al. | 239/102.2 |
| 5,527,273 A | 6/1996 | Manna et al. | |
| 5,540,656 A | 7/1996 | Pflueger et al. | |
| 5,542,917 A * | 8/1996 | Nita et al. | 604/22 |
| 5,597,882 A | 1/1997 | Schiller et al. | |
| 5,607,421 A | 3/1997 | Jeevanandam et al. | |
| 5,611,807 A | 3/1997 | O'Boyle | |
| 5,618,266 A | 4/1997 | Liprie | |
| 5,626,593 A | 5/1997 | Imran | |
| 5,658,282 A | 8/1997 | Daw et al. | |
| 5,695,460 A | 12/1997 | Siegel et al. | |
| 5,695,507 A | 12/1997 | Auth et al. | |
| 5,715,825 A | 2/1998 | Crowley | |
| 5,720,724 A | 2/1998 | Ressemann et al. | |
| 5,728,062 A | 3/1998 | Brisken | |
| 5,738,100 A | 4/1998 | Yagami et al. | |
| 5,797,876 A | 8/1998 | Spears et al. | |
| 5,816,923 A | 10/1998 | Milo et al. | |
| 5,827,203 A | 10/1998 | Nita | |
| 5,830,222 A | 11/1998 | Makower | |
| 5,895,397 A | 4/1999 | Jang et al. | |
| 5,902,287 A | 5/1999 | Martin | |
| 5,935,142 A | 8/1999 | Hood | |
| 5,944,737 A | 8/1999 | Tsonton et al. | |
| 5,957,882 A | 9/1999 | Nita et al. | |
| 5,957,899 A | 9/1999 | Spears et al. | |
| 5,964,223 A | 10/1999 | Baran | |
| 5,967,984 A | 10/1999 | Chu et al. | |
| 5,971,949 A | 10/1999 | Levin et al. | |
| 5,976,119 A | 11/1999 | Spears et al. | |
| 5,989,208 A * | 11/1999 | Nita | 604/22 |
| 5,997,497 A | 12/1999 | Nita et al. | |
| 6,004,280 A | 12/1999 | Buck et al. | |
| 6,007,499 A | 12/1999 | Martin et al. | |
| 6,007,514 A | 12/1999 | Nita | |
| 6,030,357 A | 2/2000 | Daoud et al. | |
| 6,051,010 A | 4/2000 | DiMatteo et al. | |
| 6,113,558 A | 9/2000 | Rosenschein et al. | |
| 6,123,698 A | 9/2000 | Spears et al. | |
| 6,149,596 A | 11/2000 | Bancroft | |
| 6,165,127 A | 12/2000 | Crowley | |
| 6,165,188 A | 12/2000 | Saadat et al. | |
| 6,179,809 B1 | 1/2001 | Khairkhahan et al. | |
| 6,190,353 B1 | 2/2001 | Makower et al. | |
| 6,206,842 B1 | 3/2001 | Tu et al. | |
| 6,210,356 B1 | 4/2001 | Anderson et al. | |
| 6,217,543 B1 | 4/2001 | Anis et al. | |
| 6,231,546 B1 | 5/2001 | Milo et al. | |
| 6,231,587 B1 | 5/2001 | Makower | |
| 6,235,007 B1 | 5/2001 | Divino, Jr. et al. | |
| 6,241,692 B1 | 6/2001 | Tu et al. | |
| 6,241,703 B1 | 6/2001 | Levin et al. | |
| 6,277,084 B1 | 8/2001 | Abele et al. | |
| 6,283,983 B1 | 9/2001 | Makower et al. | |
| 6,287,271 B1 | 9/2001 | Dubrul et al. | |
| 6,287,285 B1 | 9/2001 | Michal et al. | |
| 6,287,317 B1 | 9/2001 | Makower et al. | |
| 6,296,620 B1 | 10/2001 | Gesswein et al. | |
| 6,302,875 B1 | 10/2001 | Makower et al. | |
| 6,315,741 B1 | 11/2001 | Martin et al. | |
| 6,379,378 B1 | 4/2002 | Werneth et al. | |
| 6,387,109 B1 | 5/2002 | Davison et al. | |
| 6,394,956 B1 | 5/2002 | Chandrasekaran et al. | |
| 6,398,736 B1 | 6/2002 | Seward | |
| 6,416,533 B1 | 7/2002 | Gobin et al. | |
| 6,423,026 B1 | 7/2002 | Gesswein et al. | |

| | | |
|---|---|---|
| 6,433,464 B2 | 8/2002 | Jones |
| 6,450,975 B1 | 9/2002 | Brennan et al. |
| 6,454,757 B1 | 9/2002 | Nita et al. |
| 6,454,997 B1 | 9/2002 | Divino, Jr. et al. |
| 6,491,707 B2 | 12/2002 | Makower |
| 6,494,891 B1 | 12/2002 | Cornish et al. |
| 6,508,781 B1 | 1/2003 | Brennan et al. |
| 6,508,784 B1 | 1/2003 | Shu |
| 6,511,458 B2 | 1/2003 | Milo et al. |
| 6,524,251 B2 | 2/2003 | Rabiner et al. |
| 6,544,215 B1 | 4/2003 | Bencini et al. |
| 6,547,754 B1 | 4/2003 | Evans et al. |
| 6,551,337 B1 | 4/2003 | Rabiner et al. |
| 6,554,846 B2 | 4/2003 | Hamilton et al. |
| 6,558,502 B2 | 5/2003 | Divino, Jr. et al. |
| 6,562,031 B2 | 5/2003 | Chandrasekaran et al. |
| 6,589,253 B1 | 7/2003 | Cornish et al. |
| 6,596,235 B2 | 7/2003 | Divino, Jr. et al. |
| 6,623,448 B2 | 9/2003 | Slater |
| 6,635,017 B1 | 10/2003 | Moehring et al. |
| 6,650,923 B1 | 11/2003 | Lesh et al. |
| 6,652,547 B2 | 11/2003 | Rabiner et al. |
| 6,660,013 B2 | 12/2003 | Rabiner |
| 6,676,900 B1 | 1/2004 | Divino, Jr. et al. |
| 6,682,502 B2 | 1/2004 | Bond et al. |
| 6,685,657 B2 | 2/2004 | Jones |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,810 B2 | 2/2004 | Peacock, III et al. |
| 6,702,750 B2 | 3/2004 | Yock |
| 6,719,725 B2 | 4/2004 | Milo et al. |
| 6,733,451 B2 | 5/2004 | Rabiner et al. |
| 6,761,698 B2 | 7/2004 | Shibata et al. |
| 6,855,123 B2 | 2/2005 | Nita |
| 6,866,670 B2 | 3/2005 | Rabiner et al. |
| 6,936,025 B1 | 8/2005 | Evans et al. |
| 6,936,056 B2 | 8/2005 | Nash et al. |
| 6,942,620 B2 | 9/2005 | Nita et al. |
| 6,942,677 B2 | 9/2005 | Nita et al. |
| 7,004,173 B2 | 2/2006 | Sparks et al. |
| 7,056,294 B2 | 6/2006 | Khairkhahan et al. |
| 7,131,983 B2 | 11/2006 | Murakami |
| 7,137,963 B2 | 11/2006 | Nita et al. |
| 7,220,233 B2 | 5/2007 | Nita et al. |
| 7,267,650 B2 | 9/2007 | Chow et al. |
| 7,335,180 B2 | 2/2008 | Nita et al. |
| 7,384,407 B2 | 6/2008 | Rodriguez et al. |
| 7,425,198 B2 | 9/2008 | Moehring et al. |
| 7,494,468 B2 | 2/2009 | Rabiner et al. |
| 7,503,895 B2 | 3/2009 | Rabiner et al. |
| 7,540,852 B2 | 6/2009 | Nita et al. |
| 7,604,608 B2 | 10/2009 | Nita et al. |
| 7,621,929 B2 | 11/2009 | Nita et al. |
| 7,771,358 B2 | 8/2010 | Moehring et al. |
| 2003/0009153 A1 | 1/2003 | Brisken et al. |
| 2003/0036705 A1 | 2/2003 | Hare et al. |
| 2003/0199817 A1 | 10/2003 | Thompson et al. |
| 2003/0216732 A1 | 11/2003 | Truckai et al. |
| 2003/0225332 A1 | 12/2003 | Okada et al. |
| 2005/0215946 A1 | 9/2005 | Hansmann et al. |
| 2005/0228286 A1 | 10/2005 | Messerly et al. |
| 2006/0206039 A1 | 9/2006 | Wilson et al. |
| 2006/0264809 A1 | 11/2006 | Hansmann et al. |
| 2007/0260172 A1 | 11/2007 | Nita |
| 2008/0221506 A1 | 9/2008 | Rodriguez et al. |
| 2008/0228111 A1 | 9/2008 | Nita |
| 2011/0130834 A1 | 6/2011 | Wilson et al. |

FOREIGN PATENT DOCUMENTS

| | | |
|---|---|---|
| DE | 2438648 | 2/1976 |
| DE | 3821836 | 1/1990 |
| DE | 4042435 | 8/1991 |
| EP | 0005719 | 12/1979 |
| EP | 0316789 | 5/1989 |
| EP | 0376562 | 7/1990 |
| EP | 0379156 | 7/1990 |
| EP | 0394583 | 10/1990 |
| EP | 0443256 | 8/1991 |
| EP | 0541249 | 5/1993 |
| EP | 0820728 | 1/1998 |
| GB | 1106957 | 3/1968 |
| JP | 01099547 | 4/1989 |
| JP | U03067608 | 7/1991 |
| JP | 2006086822 | 3/1994 |
| JP | 2007116260 | 5/1995 |
| JP | 10216140 | 8/1998 |
| JP | 2001104356 | 4/2001 |
| JP | 2001321388 | 11/2001 |
| JP | 2002186627 | 7/2002 |
| WO | WO8906515 | 7/1989 |
| WO | WO9001300 | 2/1990 |
| WO | WO9004362 | 5/1990 |
| WO | WO9107917 | 6/1991 |
| WO | WO9211815 | 7/1992 |
| WO | WO9308750 | 5/1993 |
| WO | WO9316646 | 9/1993 |
| WO | WO9412140 | 6/1994 |
| WO | WO9414382 | 7/1994 |
| WO | WO9508954 | 4/1995 |
| WO | WO9509571 | 4/1995 |
| WO | WO9635469 | 11/1996 |
| WO | WO9745078 | 12/1997 |
| WO | WO9925412 | 5/1999 |
| WO | WO0053341 A1 | 9/2000 |
| WO | WO00/67830 | 11/2000 |
| WO | WO2004012609 | 2/2004 |
| WO | WO2004112888 | 12/2004 |

OTHER PUBLICATIONS

Extended European Search Report dated Mar. 5, 2012 for European Application No. 12153606.4.

* cited by examiner

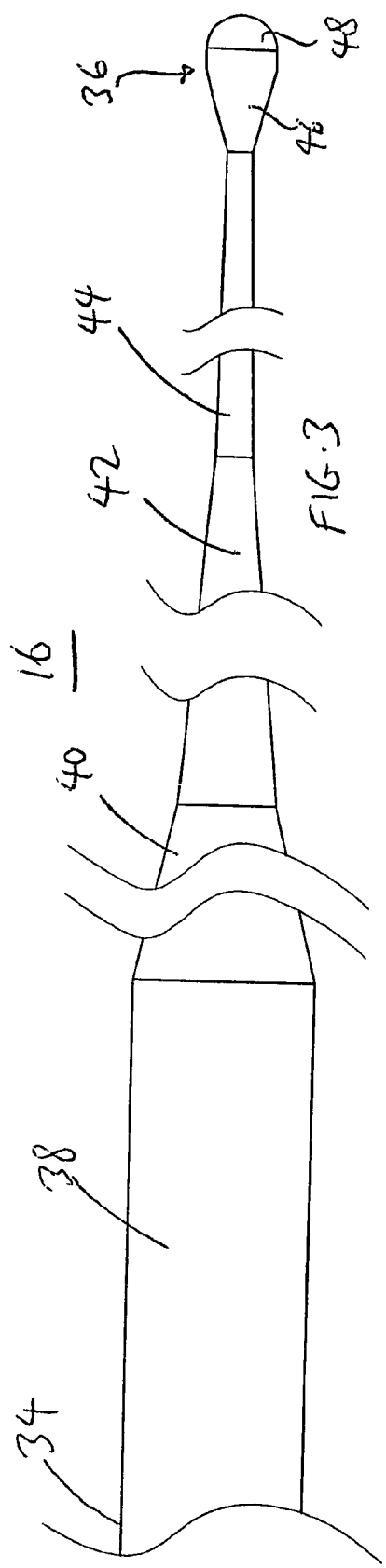
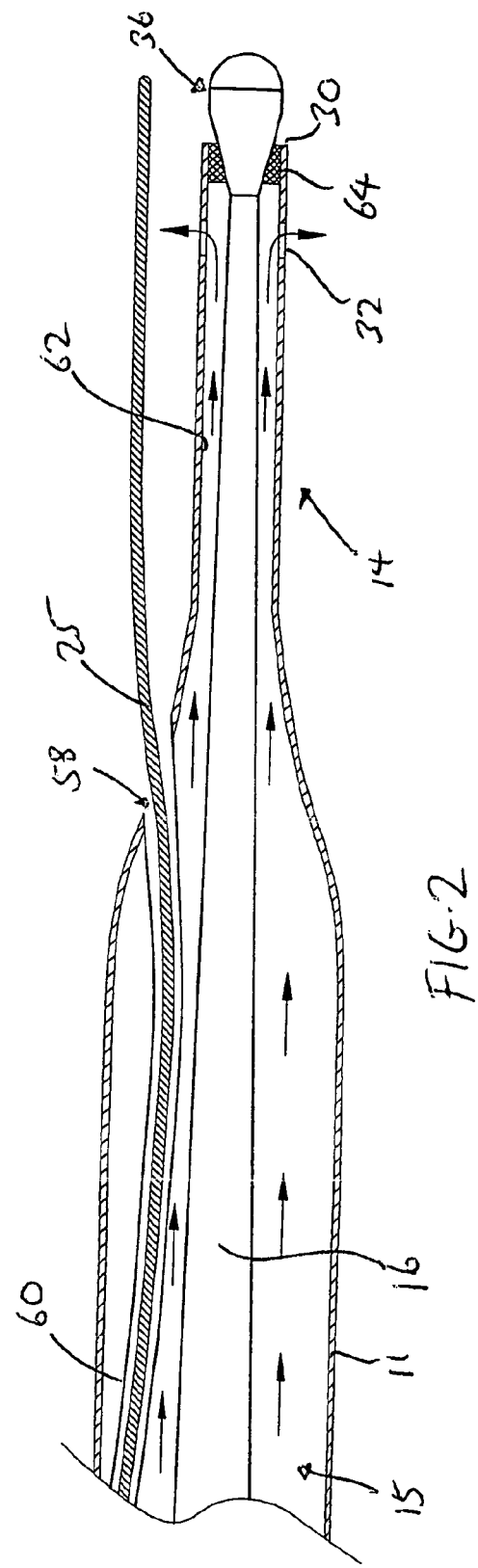

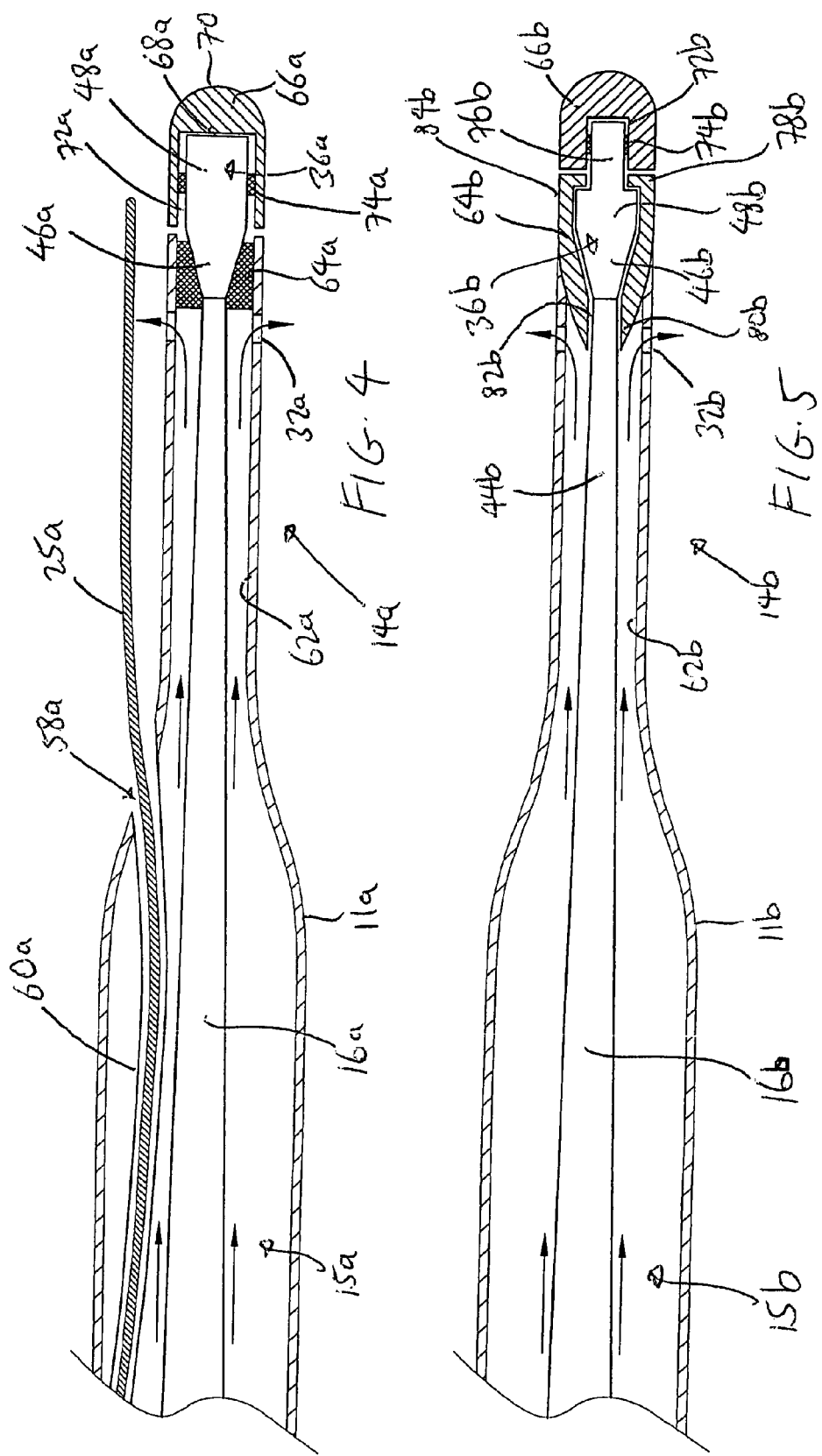

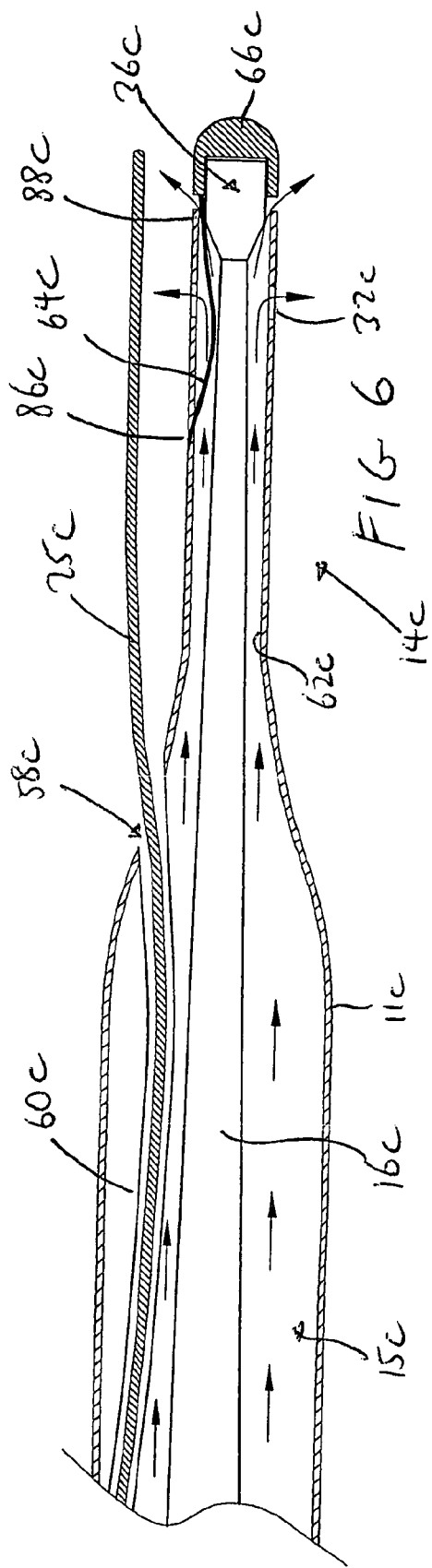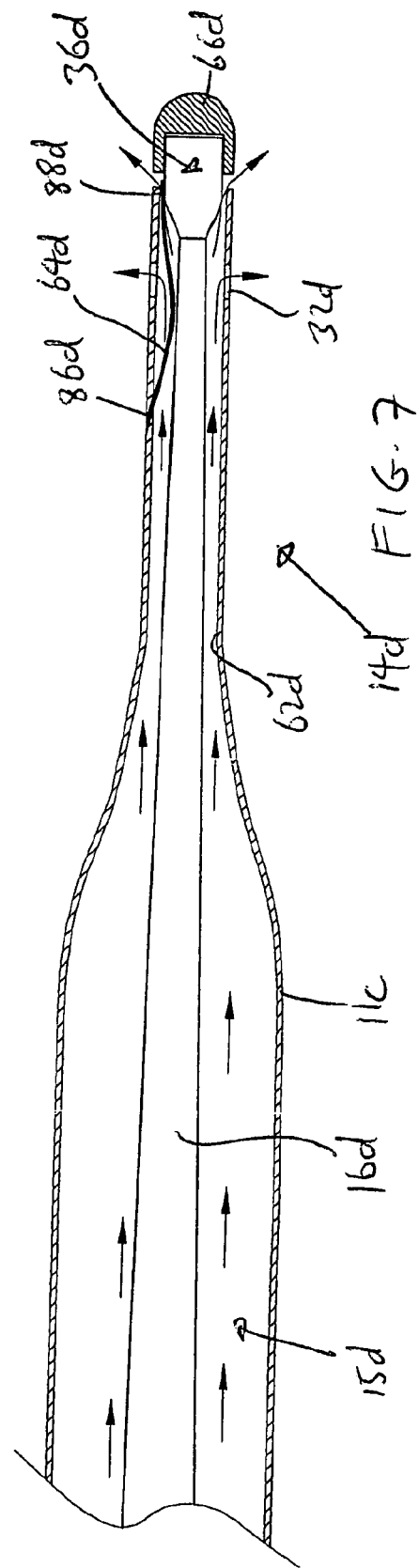

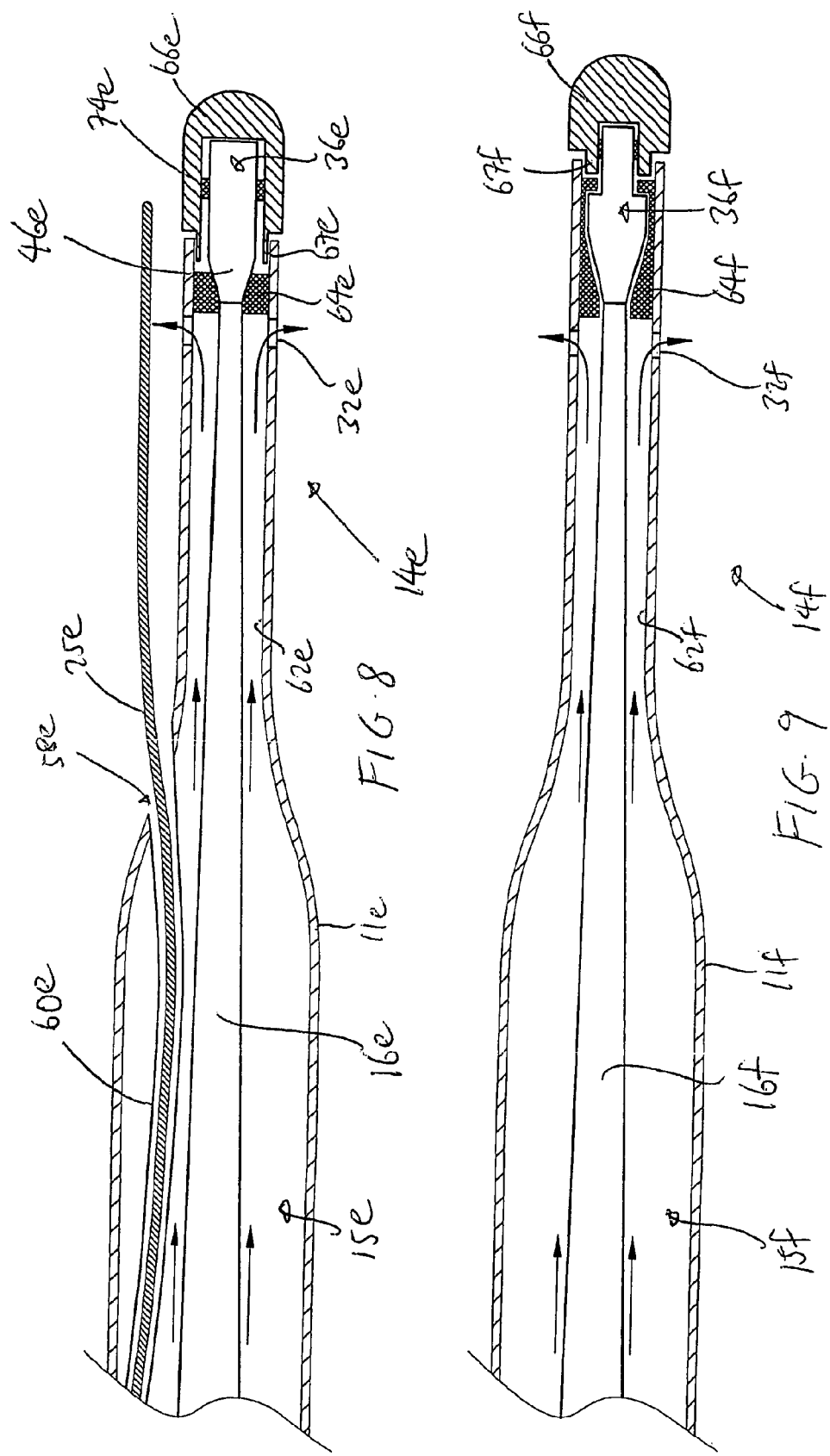

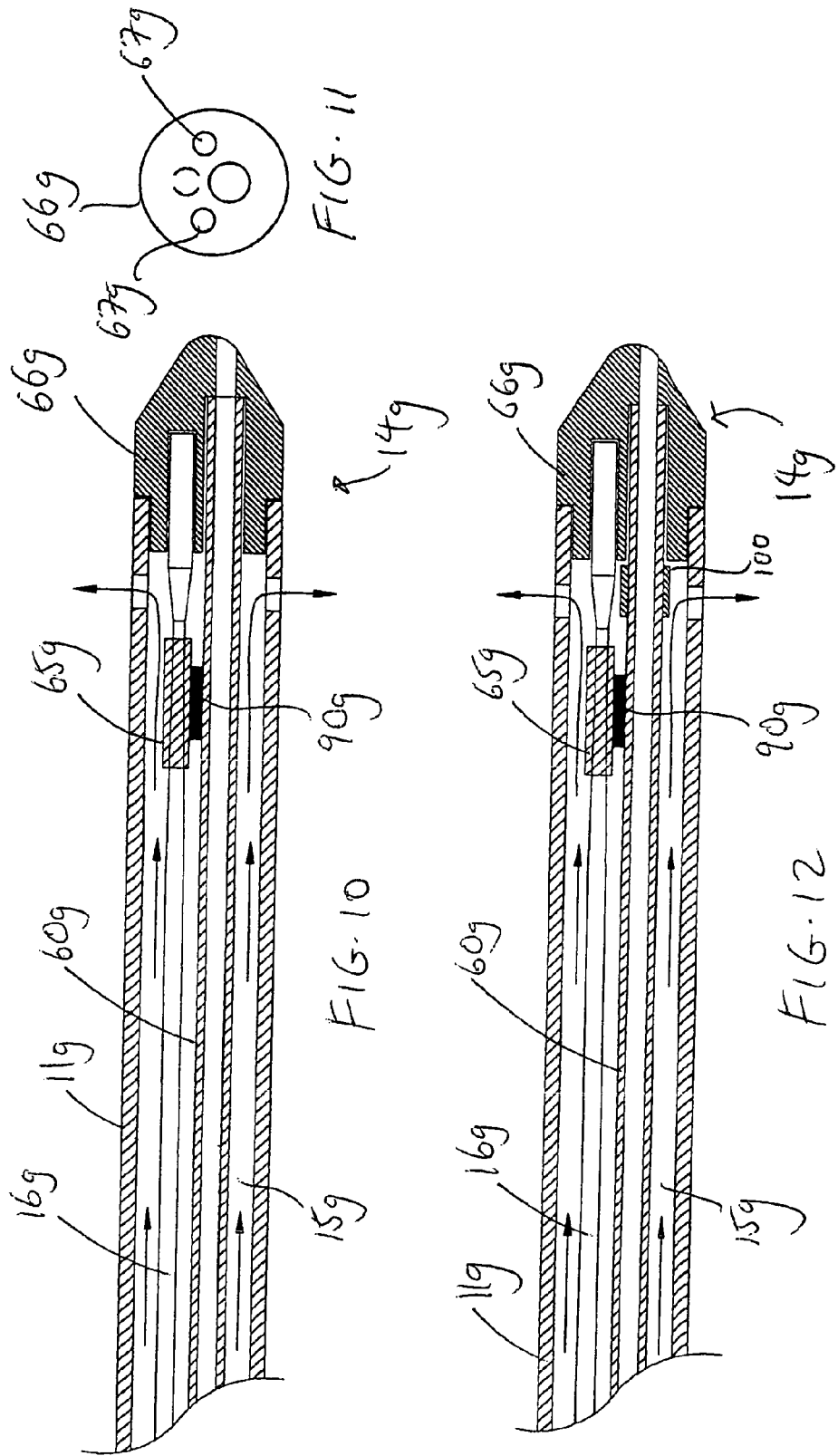

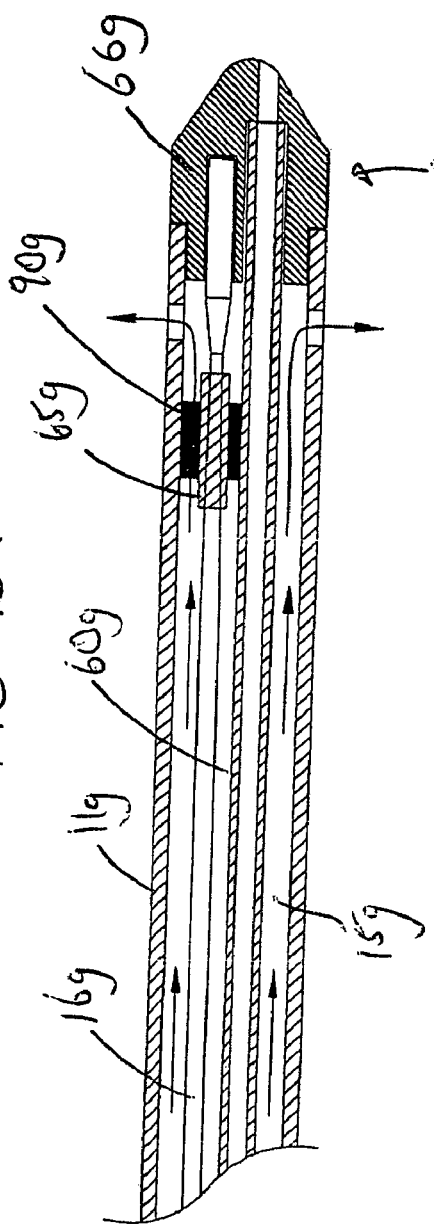
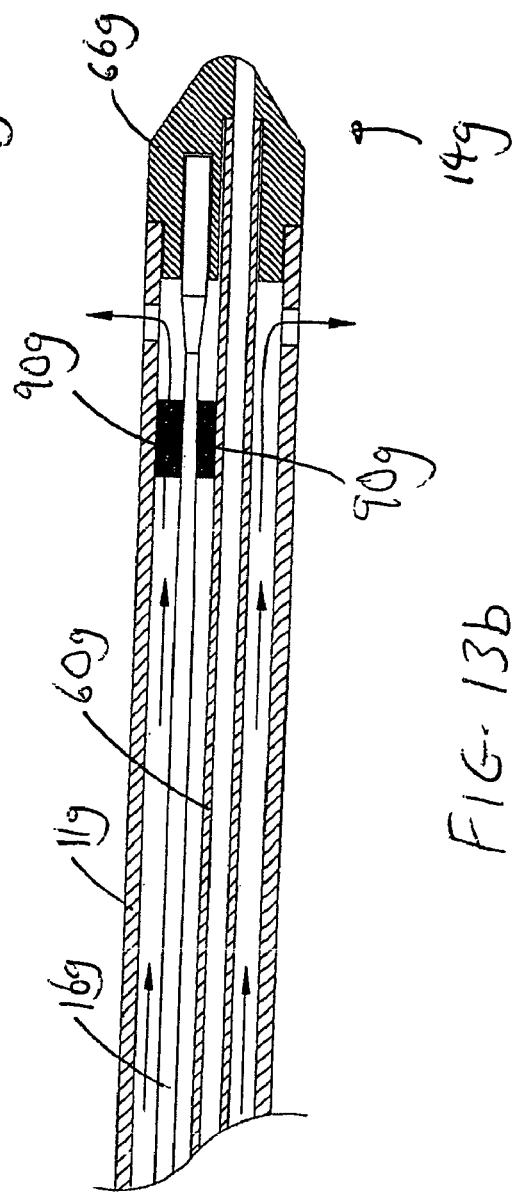

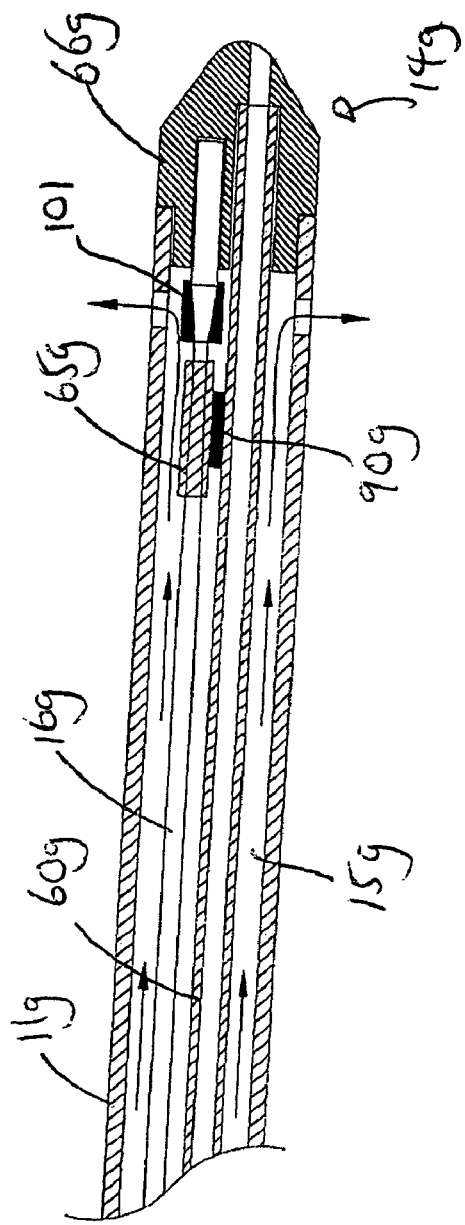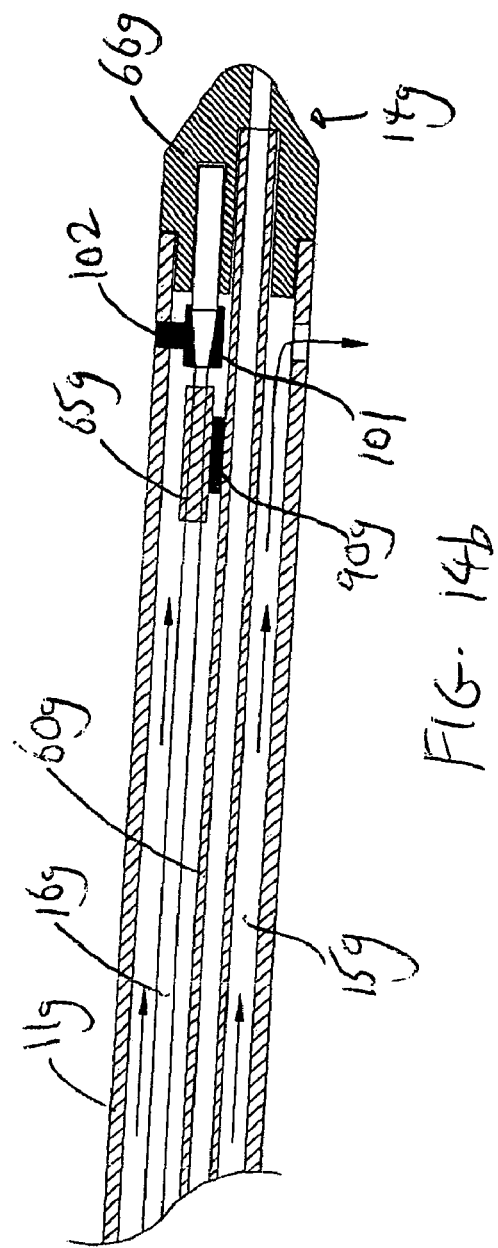

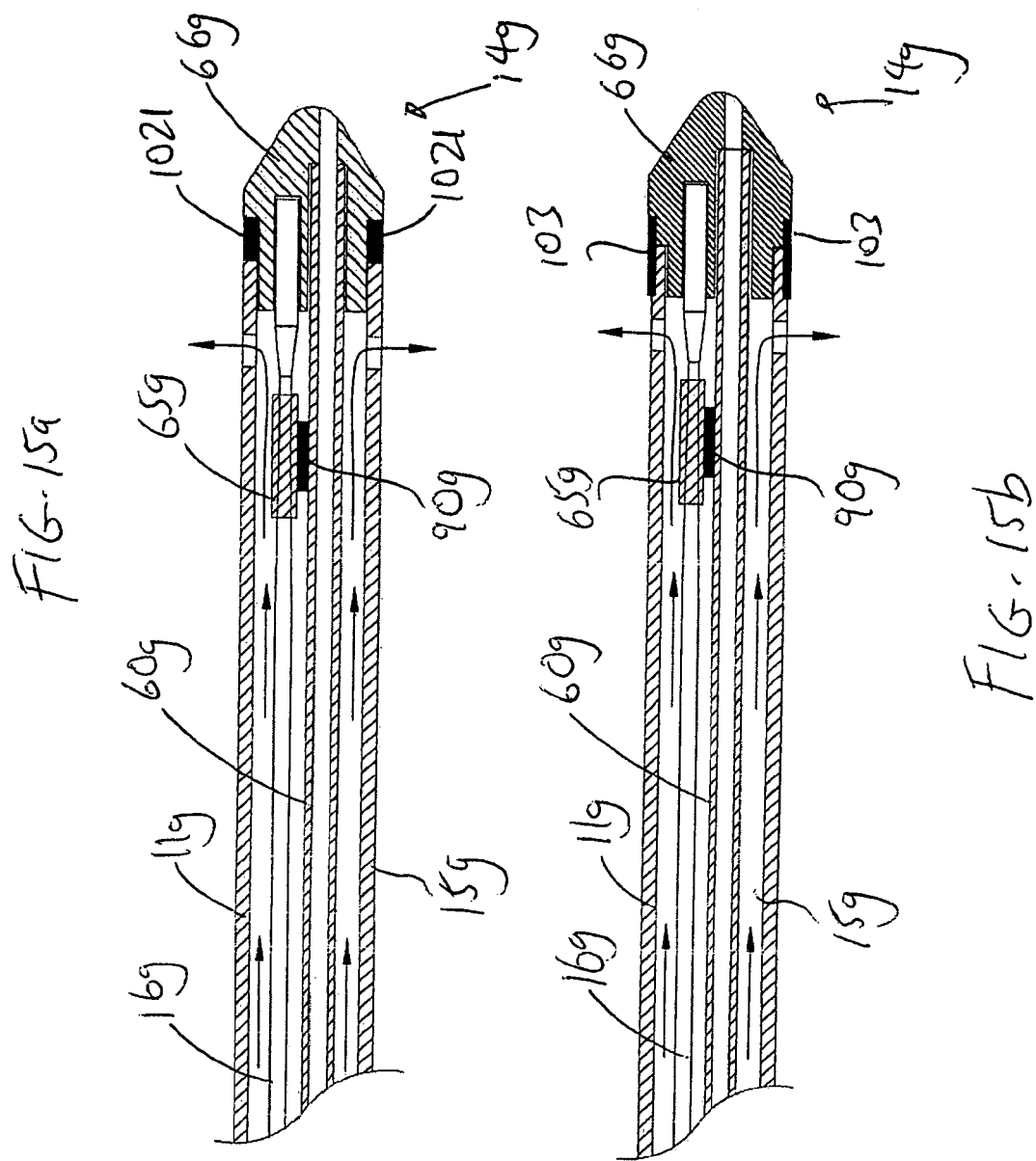

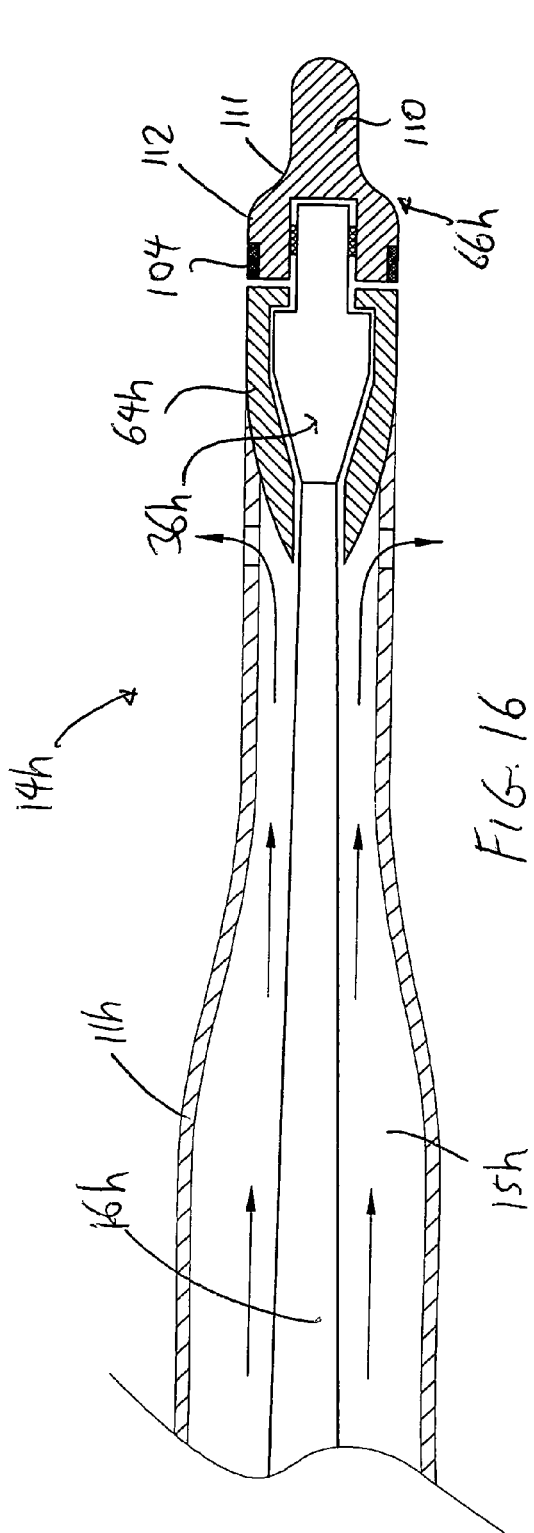
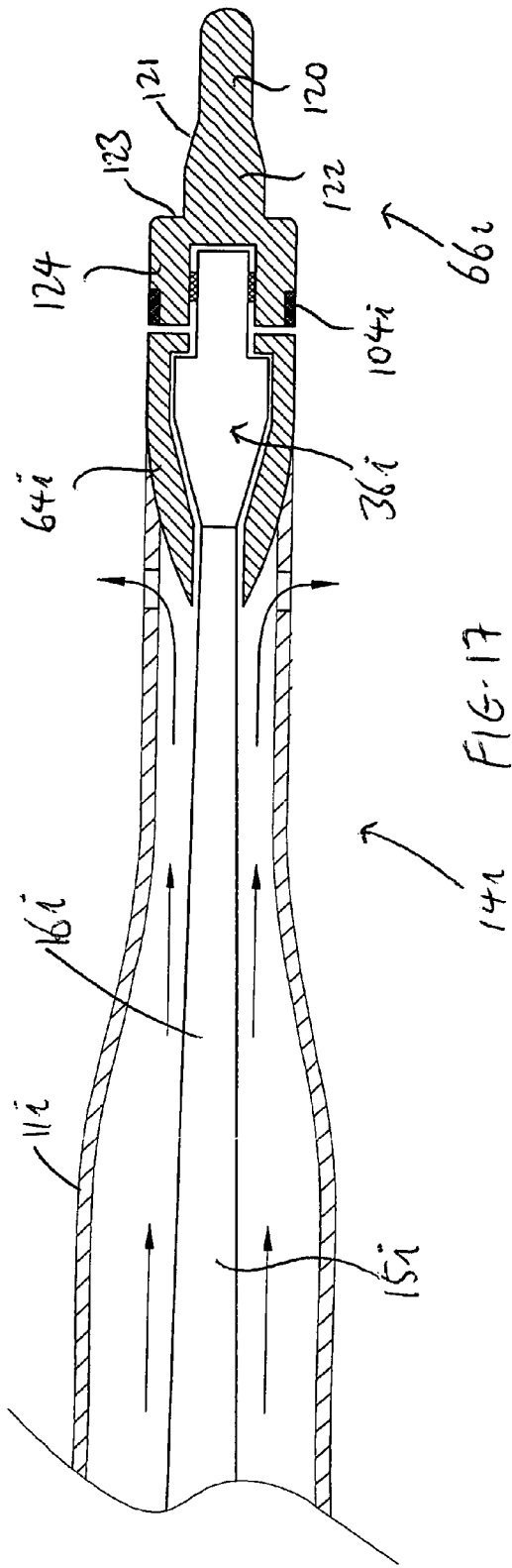

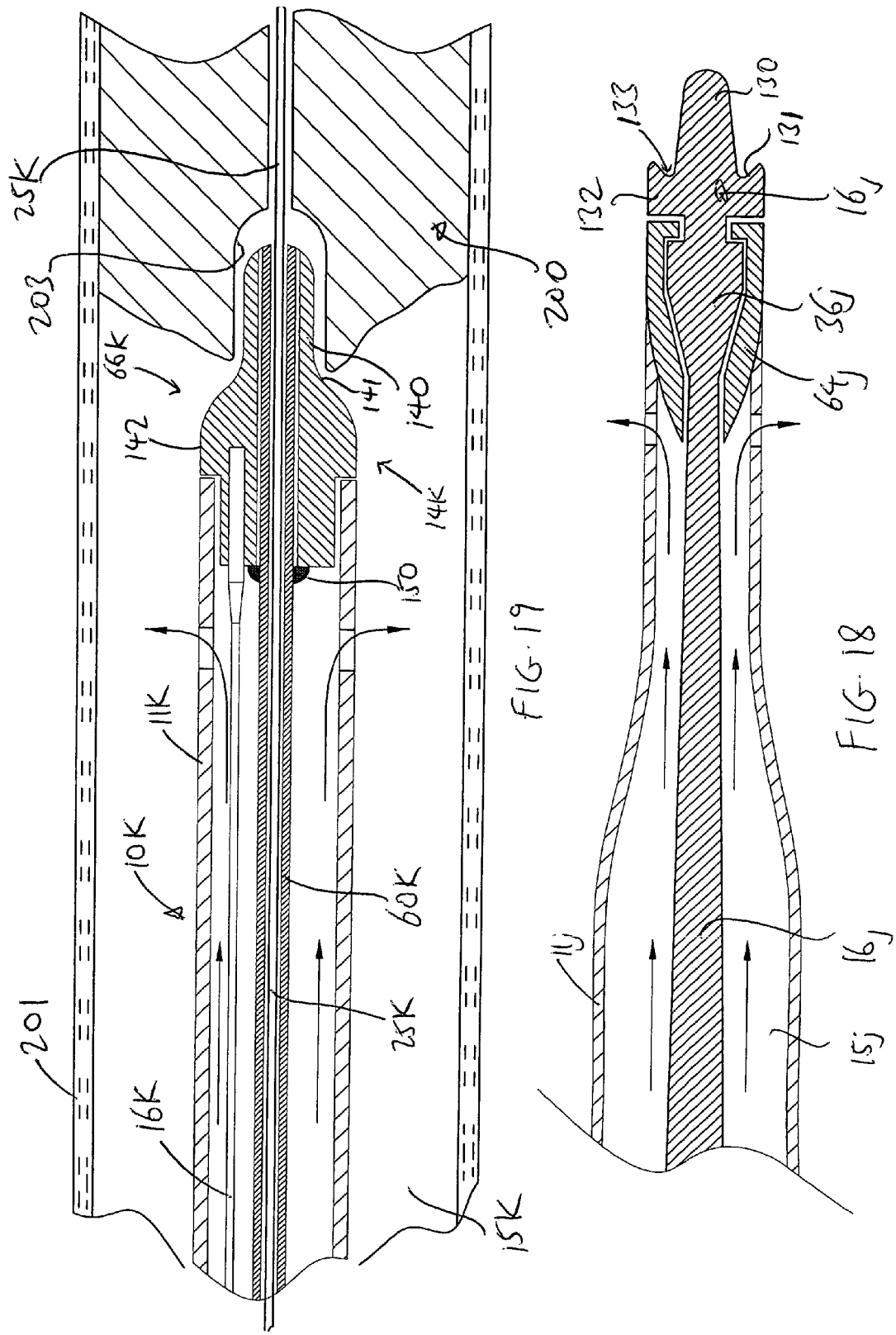

ULTRASOUND CATHETER HAVING IMPROVED DISTAL END

RELATED CASES

This is a continuation-in-part of Ser. No. 12/004,984, filed Dec. 21, 2007, which is in turn a continuation-in-part of Ser. No. 11/594,663, filed Nov. 7, 2006, now U.S. Pat. No. 8,133,236 whose entire disclosures are incorporated herein by this reference as though set forth fully herein.

BACKGROUND OF THE INVENTION

1. Field of the Invention

The present invention pertains to medical equipment, and more particularly, to a therapeutic ultrasound system for ablating obstructions within tubular anatomical structures such as blood vessels. The ultrasound system includes a protective feature that minimizes the introduction of debris into the patient's vasculature if the ultrasound transmission member were to break, fracture or become dislodged during a medical procedure. The ultrasound system also includes a distal tip configuration that increases energy intensity and reduces perforations.

2. Description of the Prior Art

A number of ultrasound systems and devices have heretofore been proposed for use in ablating or removing obstructive material from blood vessels. Ultrasound catheters have been utilized to ablate various types of obstructions from blood vessels of humans and animals. Successful applications of ultrasound energy to smaller blood vessels, such as the coronary arteries, requires the use of relatively small diameter ultrasound catheters which are sufficiently small and flexible to undergo transluminal advancement through the tortuous vasculature of the aortic arch and coronary tree. However, because of its small diameter, the ultrasound transmission member which extends through such catheters is particularly susceptible to losses in the transmitted ultrasound energy, and breakage. Reducing the size of the ultrasound transmission member, particularly the distal tip, will increase energy intensity. However, it will also make the distal tip of the ultrasound transmission member more prone to perforations due to inherited stiffness of the transmission member and a smaller tip size.

Breakage of ultrasound transmission members often occurs near the proximal end thereof, generally at the coupling between the ultrasound catheter coupling and the ultrasound transducer. This is believed to be because energy concentrations and stresses are highest at these points. Thus, any external forces applied to the ultrasound transmission member in this region may result in stresses exceeding the elastic limit of the ultrasound transmission member.

Breakage of ultrasound transmission members can also occur near the distal end thereof, generally at the area of the smallest cross-section. To minimize breakage of the ultrasound transmission wire at the distal end, a smaller distal tip with less mass or a tip made of polymer or a lower density metal may be utilized to further reduce stress at the distal in on the transmission wire. It is important that any debris resulting from the breakage of the ultrasound transmission member not be allowed to be introduced into a patient's vasculature during a medical procedure.

Thus, there still exists a need to further improve efficacy of the ultrasound systems and protect against breakage of the ultrasound transmission member during a medical procedure.

SUMMARY OF THE DISCLOSURE

It is an object of the present invention to provide an ultrasound catheter system with a protective feature that prevents or minimizes the introduction of debris into the patient's vasculature if the ultrasound transmission member were to break or fracture during a medical procedure.

In order to accomplish the objects of the present invention, there is provided an ultrasound catheter having an elongate flexible catheter body having a lumen extending longitudinally therethrough, and an ultrasound transmission member extending longitudinally through the lumen of the catheter body. The ultrasound transmission member has a proximal end that is coupled to a separate ultrasound generating device, and a distal end that terminates at the distal end of the catheter body. The ultrasound transmission member is directly attached to the guidewire tube and/or the catheter body, and such attachment can be accomplished using a direct attachment or via an attachment member. A radiopaque marker or sleeve can also be positioned on the distal end of the ultrasound catheter to improve its visibility.

BRIEF DESCRIPTION OF THE DRAWINGS

FIG. 2 is a cross-sectional view of the distal end of an ultrasound catheter that can be used with the system of FIG. 1 according to one embodiment thereof.

FIG. 3 is a side sectional view of an ultrasound transmission member that can be used with the system of FIG. 1.

FIGS. 4-9 are cross-sectional views of the distal end of various ultrasound catheters that can be used with the system of FIG. 1 according to different embodiments thereof.

FIG. 10 illustrates the distal end of an ultrasound catheter according to another embodiment of the present invention that can be used with the system of FIG. 1, where the ultrasound transmission member is attached to the guidewire tube.

FIG. 11 is a front view of the distal end of the catheter of FIG. 10.

FIG. 12 illustrates a modification that can be made to the ultrasound catheter of FIG. 10 with a radiopaque marker located on the distal portion of the guidewire lumen.

FIGS. 13*a* and 13*b* illustrate a modification that can be made to the ultrasound catheter of FIG. 10 with the ultrasound transmission member attached to the guidewire tube and the catheter body.

FIGS. 14*a* and 14*b* illustrate a modification that can be made to the ultrasound catheter of FIG. 10 with a radiopaque marker located on the distal portion of the ultrasound transmission member.

FIGS. 15*a* and 15*b* illustrate a modification that can be made to the ultrasound catheter of FIG. 10 with a radiopaque marker positioned on the distal tip and a radiopaque marker positioned partially on the catheter body and partially on the distal tip.

FIGS. 16-18 illustrate modifications that can be made to the ultrasound catheter in FIG. 5.

FIG. 19 illustrates modifications that can be made to the ultrasound catheter of FIG. 10.

DETAILED DESCRIPTION OF THE PREFERRED EMBODIMENTS

Figure 1:
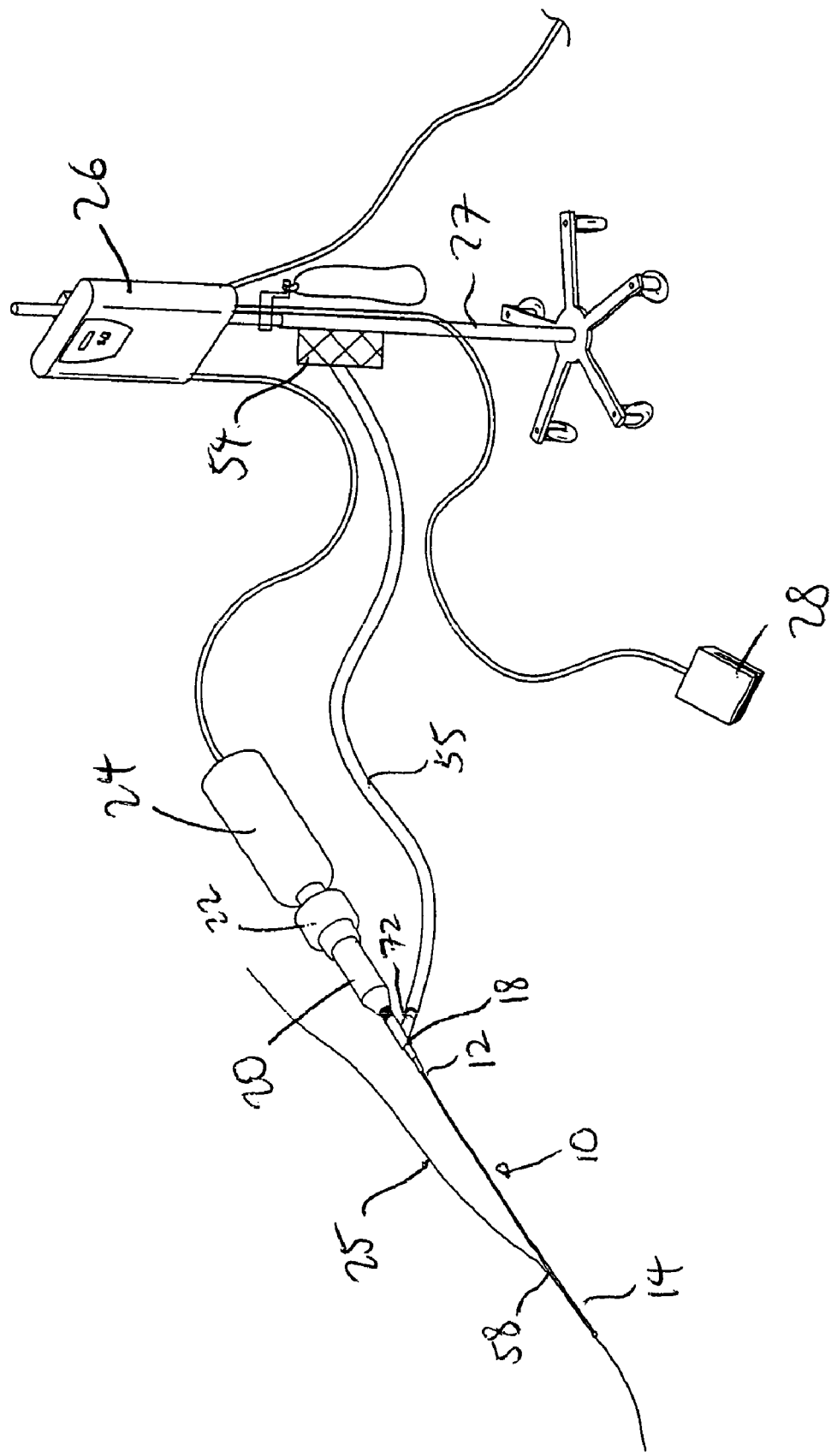
FIG. 1 is a perspective view of an ultrasound system according to the present invention.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

FIG. 1 illustrates an ultrasound system according to the present invention for use in ablating and removing occlusive material inside the vessel of an animal or human. Referring to FIGS. 1 and 2, the ultrasound system includes an ultrasound catheter device 10 which has an elongate catheter body 11 having a proximal end 12, a distal end 14, and defining at least one lumen 15 extending longitudinally therethrough. The ultrasound catheter device 10 is operatively coupled at its proximal end 12, by way of a Y-connector 18, a catheter knob 20, and a slide collar 22, to an ultrasound transducer 24. The ultrasound transducer 24 is connected to a signal generator 26, which can be provided with a foot actuated on-off switch 28. The signal generator 26 can be supported by an IV pole 27. When the on-off switch 28 is depressed, the signal generator 26 sends an electrical signal to the ultrasound transducer 24, which converts the electrical signal to ultrasound energy. Such ultrasound energy subsequently passes through the catheter device 10 and is delivered to the distal end 14. A guidewire 25 may be utilized in conjunction with the catheter device 10, as will be more fully described below.

The catheter body 11 is formed of a flexible polymeric material such as nylon (Pebax™) manufactured by Atochimie, Cour be Voie, Hauts Ve-Sine, France. The flexible catheter body 11 is preferably in the form of an elongate tube having one or more lumens extending longitudinally therethrough. The catheter body 11 defines a main lumen 15. Extending longitudinally through the main lumen 15 is an elongate ultrasound transmission member 16 having a proximal end which is removably connectable to the ultrasound transducer 24 via a sonic connector (not shown) such that ultrasound energy will pass through the ultrasound transmission member 16. As such, when the foot actuated on-off switch 28 operatively connected to the ultrasound transducer 24 is depressed; ultrasound energy will pass through the ultrasound transmission member 16 to the distal end 14 of the catheter body 11.

A guidewire port 58 is provided in the catheter body 11 at any location along the catheter body 11. A guidewire lumen 60 extends from the guidewire port 58 through the main lumen 15 of the catheter body 11 in a manner that is concomitant to the length of the ultrasound transmission member 16. In one embodiment, the guidewire port 58 can be provided at a location that is closer to the proximal end 12 than to the distal end 14 of the catheter.

In one embodiment, the ultrasound transmission member 16 may be formed of any material capable of effectively transmitting the ultrasonic energy from the ultrasound transducer 24 to the distal end 14 of the ultrasound transmission member 16, and is preferably made from metal or metal alloys. It is possible to form all or a portion of the ultrasound transmission member 16 with one or more materials which exhibit super-elasticity. Such materials should preferably exhibit super-elasticity consistently within the range of temperatures normally encountered by the ultrasound transmission member 16 during operation of the catheter device 10. Specifically, all or part of the ultrasound transmission member 16 may be formed of one or more metal alloys known as "shape memory alloys". Examples of super-elastic metal alloys which are usable to form the ultrasound transmission member 16 of the present invention are described in detail in U.S. Pat. Nos. 4,665,906 (Jervis); 4,565,589 (Harrison); 4,505,767 (Quin); and 4,337,090 (Harrison). The disclosures of U.S. Pat. Nos. 4,665,906; 4,565,589; 4,505,767; and 4,337,090 are expressly incorporated herein by reference insofar as they describe the compositions, properties, chemistries, and behavior of specific metal alloys which are super-elastic within the temperature range at which the ultrasound transmission member 16 of the present invention operates, any and all of which super-elastic metal alloys may be usable to form the super-elastic ultrasound transmission member 16.

The frontal portion of the Y-connector 18 is connected to the proximal end 12 of the catheter 10 using techniques that are well-known in the catheter art. An injection pump 54 or IV bag (not shown) or syringe (not shown) can be connected, by way of an infusion tube 55, to an infusion port or sidearm 72 of the Y-connector 18 (see FIG. 1). The injection pump can be used to infuse coolant fluid into and/or through the main lumen 15 of the catheter 10, with the coolant fluid exiting via irrigation outlets 32 (see FIG. 2) provided adjacent the distal end 14 of the catheter 10. Such flow of coolant fluid may be utilized to prevent overheating of the ultrasound transmission member 16 extending longitudinally through the main lumen 15. Such flow of the coolant fluid through the main lumen 15 of the catheter 10 also serves to bathe the outer surface of the ultrasound transmission member 16, thereby providing for an equilibration of temperature between the coolant fluid and the ultrasound transmission member 16. Thus, the temperature and/or flow rate of coolant fluid may be adjusted to provide adequate cooling and/or other temperature control of the ultrasound transmission member 16. The irrigation fluid can include a pharmacological agent and/or microbubbles.

In addition to the foregoing, the injection pump 54 or syringe may be utilized to infuse a radiographic contrast medium into the catheter 10 for purposes of imaging. Examples of iodinated radiographic contrast media which may be selectively infused into the catheter 10 via the injection pump 54 are commercially available as Angiovist 370 from Berlex Labs, Wayne, N.J. and Hexabrix from Malinkrodt, St. Louis, Mo.

The proximal end of the Y-connector 18 is attached to the distal end of the catheter knob 20 by threadably engaging the proximal end of the Y-connector 18 inside a threaded distal bore (not shown) at the distal end of the catheter knob 20.

The proximal end of the ultrasound transmission member 16 is attached to a sonic connector (not shown) which is configured to effect operative and removable attachment of the proximal end of the ultrasound transmission member 16 to the horn of the ultrasound transducer 24. The sonic connector is preferably configured and constructed to permit passage of ultrasound energy through the ultrasound transmission member 16 with minimal lateral side-to-side movement of the ultrasound transmission member 16 while, at the same time, permitting unrestricted longitudinal forward/backward vibration or movement of the ultrasound transmission member 16. Examples of ultrasound transducers, sonic connectors and their connections are illustrated in U.S. Pat. Nos. 6,702,748, 6,855,123, 6,942,620 and 6,942,677, whose disclosures are incorporated by this reference as though set forth fully herein.

Referring to FIGS. 2 and 3, the ultrasound transmission member 16 can have progressively tapered regions extending from the proximal end 34 thereof to the distal tip 36 thereof. For example, the proximal-most region 38 can have a constant diameter which is the greatest diameter along the length of the ultrasound transmission member 16. The region 38 transitions at its distal end to a first tapered region 40 which gradually decreases in diameter to its distal end to a second tapered region 42, which gradually decreases in diameter to its distal end to a third tapered region 44, which gradually decreases in diameter to its distal end to the distal tip 36. Each tapered region 40, 42, 44 can have a continuous taper, and be tapered to different degrees, such that the region 40 has a greater taper than the region 42, which in turn has a greater taper than the region 44. The distal-most part of the region 44 can have the smallest diameter along the entire ultrasound transmission member 16. The continuously decreasing tapering from the proximal to the distal direction shown in FIG. 3 allows for improved ultrasound energy propagation. The distal tip 36 can have a proximal section 46 which gradually increases in diameter until it reaches the proximal end of a distal section 48. The distal section 48 can have a bulbous configuration having a rounded or curved distal-most end that is adapted to contact the obstruction for ablation thereof. Thus, the distal tip 36 can have an enlarged size when compared to the rest of the ultrasound transmission member 16 so that the distal tip 36 can function as the distal head for the catheter 10.

In the embodiment shown in FIG. 2, the distal end 14 of the catheter body 11 has an opening 30, and the distal tip 36 of the ultrasound transmission member 16 is secured to the inner wall 62 of the main lumen 15 of the catheter body 11 adjacent the opening 30. The securement can be accomplished by an attachment mechanism 64 (which can be glue, welding or fusing) at the location of the proximal section 46 and the inner wall 62, so that part of the proximal section 46 is received inside the main lumen 15 and with the distal section 48 of the distal tip 36 extending outside the main lumen 15 of the catheter body 11. The opening 30 of the catheter body 11 is closed by the connection of the distal tip 36 to the catheter body 11. The construction shown in FIG. 2 directly attaches the ultrasound transmission member 16 to the catheter body 11 (via the attachment mechanism 64), which provides additional protection if the ultrasound transmission member 16 experiences breakage. In particular, if the ultrasound transmission member 16 fractures, breaks or splinters, the distal tip 36 will still remain secured to the catheter body 11 via the attachment device 64, and will not become dislodged from the catheter body 11. Thus, the embodiment of FIG. 2 does not employ a separate distal head for the catheter 10, but instead utilizes the distal tip 36 of the ultrasound transmission member 16 as a distal head which is secured directly to the distal end of the catheter body 11.

FIGS. 4-5 illustrate two different embodiments of a distal end of the catheter 10 which utilize the same principles and general construction as in FIG. 2, except that a distal cap is secured to the distal tip of the ultrasound transmission member. Therefore, the same numeral designations are used in FIGS. 2, 4 and 5 to designate the same or similar elements, except that an "a" and a "b" are added to the numeral designations in FIGS. 4 and 5, respectively. The differences between the embodiment of FIG. 2 and the embodiments in FIGS. 4 and 5 are described below.

The distal end 14a in FIG. 4 differs from the distal end 14 in FIG. 2 in that a protective cap 66a is secured to the distal section 48a of the distal tip 36a of the ultrasound transmission member 16a. The cap 66a can function as the tip of the catheter 10. The distal tip 36a itself has a different configuration from the distal tip 36 in FIG. 2 in that the distal section 48a is not bulbous or curved, but instead has a constant diameter that terminates distally at a flat distal end 68a. The cap 66a has a cylindrical configuration with an opened proximal end and a curved or bulbous distal end 70a. The distal section 48a of the distal tip 36a is received into the hollow bore 72a of the cap 66a via the opened proximal end of the cap 66a, and is secured to the cap 66a inside the bore 72a via an attachment device 74a (which can be the same as the attachment device 64). The cap 66a can be made of a radiopaque material to improve the visibility of the distal tip 36a.

In addition, instead of the attachment mechanism 64, the embodiments of FIGS. 4-5 provide an intermediate member 64a. The intermediate member 64a can be a cylindrical component that is positioned around the ultrasound transmission member 16a, and between the ultrasound transmission member 16a and the inner wall 62a of the catheter body 11a. The intermediate member 64a (as well as 64 and 64b) is preferably made from a material that does not effectively transfer or conduct heat, and which is easy to attach to the ultrasound transmission member 16a and the catheter body 11a. Examples of the material can include certain epoxies, polymers, plastics and rubber. According to one embodiment, the intermediate member 64a can be fused to the ultrasound transmission member 16a and the inner wall 62a. According to another embodiment, the intermediate member 64a can be bonded to the ultrasound transmission member 16a and the inner wall 62a. According to yet another embodiment, the intermediate member 64a can be fused to the ultrasound transmission member 16a and bonded to the inner wall 62a. The intermediate member 64a serves as a safety feature to hold the ultrasound transmission member 64a within the catheter body 11 in the event the ultrasound transmission member 16a experiences breakage at a location proximal to the intermediate member 64a. However, the intermediate member 64a will not be able to hold the distal tip 36a if the breakage occurs at the distal tip 36a.

The distal end 14b in FIG. 5 differs from the distal end 14a in FIG. 4 in the following ways. First, the guidewire port 58a, guidewire 25a, and guidewire lumen 60a have been omitted. Second, the distal tip 36b itself has a different configuration from the distal tip 36a in FIG. 4 in that a distal extension 76b extends distally from the distal section 48b. The distal extension 76b has a smaller constant diameter than the diameter of the enlarged distal section 48b, and the distal extension 76b is received into the hollow bore 72b of the cap 66b via the opened proximal end of the cap 66b, and is secured to the cap 66b inside the bore 72b via an attachment mechanism 74b (which can be the same as the attachment mechanism 64). The cap 66b can also be made of a radiopaque material to improve the visibility of the distal tip 36b.

Third, the intermediate member 64b in FIG. 5 has a different configuration as the intermediate member 64a. The intermediate member 64b has a generally conical configuration, having a wider diameter at its distal end 78b (which resembles the base of the cone) and a narrower diameter or dimension at its proximal end 80b (which resembles the narrowed tip of a cone). The hollow interior 82b of the intermediate member 64b has the greatest inner diameter adjacent its distal end 78b and decreases to its smallest inner diameter adjacent the proximal end 80b. This configuration for the intermediate member 64b allows the ultrasound transmission member 16b to be fitted and retained inside the hollow interior 82b without the need to directly attach the ultrasound transmission member 16b to the intermediate member 64b. Specifically, the sections 46b, 48b can be retained inside the hollow interior 82b, with the transition between the region 44b and the distal tip 36b (i.e., where the diameter of the ultrasound transmission member 16b is the smallest) received in the narrow opening of the proximal end 80b of the intermediate member 64b. In other words, the proximal end 80b overlaps a dimensional step (i.e., the transition between the region 44b and the distal tip 36b) on the ultrasound transmission member 16b. The distal extension 76b extends through another opening at the distal end 78b of the intermediate member 64b. To provide additional protection or safety, any or all of the sections 46b, 48b can also be bonded to the inner wall of the intermediate member 64b. The outer surface 84b of the intermediate member 64*b* may be attached to the opened distal end of the catheter body 11*b* by bonding, fusing or glue, and part of the intermediate member 64*b* extends beyond the distal end of the catheter body 11*b*.

Comparing the embodiments of FIGS. 4 and 5, the intermediate member 64*b* has an "overlapped" configuration, which provides added protection because the intermediate member 64*b* is seated on a dimensional step along the ultrasound transmission member 16*b*, and will always hold the proximal portions of the ultrasound transmission member 16*b* within the catheter body 11*b* as long as the intermediate member 64*b* is attached to the catheter body 11*b*.

FIG. 6 illustrates a modification that can be made to the embodiment in FIG. 4. The embodiments in FIGS. 4 and 6 utilize the same principles and general construction, so the same numeral designations are used in FIGS. 4 and 6 to designate the same or similar elements, except that a "c" is added to the numeral designations in FIG. 6.

In FIG. 6, the catheter body 11*c*, the guidewire port 58*c*, the guidewire lumen 60*c*, the guidewire 25*c*, the ultrasound transmission member 16*c* and the cap 66*c* can be the same as the catheter body 11*a*, the guidewire port 58*a*, the guidewire lumen 60*a*, the guidewire 25*a*, the ultrasound transmission member 16*a* and the cap 66*a* in FIG. 4. The primary difference is that the intermediate member 64*a* is now embodied in the form of an anchor wire 64*c*, which can be either a polymer or a metal. One end 86*c* of the wire 64*c* can be attached (e.g., by glue, fusing, bonding) to the inner wall 62*c* of the catheter body 11*c*, and the other end 88*c* of the wire 64*c* can be attached (e.g., by glue, bonding or welding) to the distal tip 36*c* and to the cap 66*c*. If the ultrasound transmission member 16*c* breaks at any location, then the ultrasound transmission member 16*c* will be retained inside the catheter body 11*c*.

FIG. 7 illustrates a modification that can be made to the embodiment in FIG. 6. Specifically, the embodiments in FIGS. 6 and 7 are the same except that the guidewire port 58*c*, the guidewire lumen 60*c* and the guidewire 25*c* are omitted in FIG. 7, and the anchor wire 64*d* is attached to the distal end of the ultrasound transmission member 16*d* but not attached to the cap 66*d*. Therefore, the same numeral designations are used in FIGS. 6 and 7 to designate the same elements, except that a "d" is added to the numeral designations in FIG. 7, and no further description of the elements in FIG. 7 is needed.

Attaching the anchor wire 64*c* or 64*d* to the cap 66*c* or 66*d*, or not attaching the anchor wire 64*c* or 64*d* to the cap 66*c* or 66*d*, provides different options. Attaching the anchor wire 64*c* to the cap 66*c* prevents dislodgement of the cap 66*c* or the distal tip 36*c* if the breakage occurs near or at the distal tip 36*c*. However, breakage at such locations is rare, so the embodiment in FIG. 7 (where the anchor wire 64*d* is not attached to the cap 66*d*) can also be employed.

FIG. 8 illustrates another modification that can be made to the embodiment in FIG. 4. Specifically, the embodiments in FIGS. 4 and 8 are the same, except that the proximal portion of the cap 66*e* has an annular edge 67*e* that extends into the interior of the catheter body 11*e*. Therefore, the same numeral designations are used in FIGS. 4 and 8 to designate the same elements, except that an "e" is added to the numeral designations in FIG. 8, and no further description of the elements in FIG. 8 is needed. The annular edge 67*e* is not attached to the catheter body 11*e*, and is maintained separate from the catheter body 11*e*. One benefit which is provided by extending a portion of the cap 66*e* into the catheter body 11*e* is that this arrangement provides a smooth and friendly transition between the distal cap 66*e* and the catheter body 11*e*. This smooth transition facilitates navigation of the distal end 14*e* through tortuous anatomy. Also, the non-affixed tip of the catheter body 11*e* can result in the improved transmission of ultrasound energy from the transducer to the distal end 14*e*.

FIG. 9 illustrates a modification that can be made to the embodiment in FIG. 5. Specifically, the embodiments in FIGS. 5 and 9 are the same except that the intermediate member 64*f* is completely retained inside the catheter body 11*f*, and the proximal portion of the cap 66*f* has an annular edge 67*f* that extends into the interior of the catheter body 11*f*. Therefore, the same numeral designations are used in FIGS. 5 and 9 to designate the same elements, except that an "f" is added to the numeral designations in FIG. 9, and no further description of the elements in FIG. 9 is needed.

A guidewire has been included in the embodiments of FIGS. 2, 4, 6 and 8, while the guidewire has been omitted in the embodiments of FIGS. 5, 7 and 9. Embodiments showing the use or omission of a guidewire are shown for reference only. The principles of the present invention may be applied to catheters that include, or not include, a guidewire. The use or omission of a guidewire depends upon the choice of the clinician, and is often dictated by the access difficulty or specific clinical situations. For example, if the target lesion is located on a straight portion of the vessel, use of a non-guidewire embodiment will be feasible and relatively easy. On the other hand, if the target lesion is located in a tortuous location of the vessel, then use of a guidewire embodiment will help the clinician to navigate the distal tip 36 to the location of the lesion.

FIGS. 10-11 illustrate a different embodiment of the present invention where the ultrasound transmission member is directly connected to the guidewire tube. Since the embodiment of FIGS. 10-11 utilize the similar principles and constructions as the other embodiments, the same numeral designations are used in FIG. 10 to designate the same elements as in the earlier embodiments, except that a "g" is added to the numeral designations. The ultrasound catheter has an elongate catheter body 11*g*, and at least one lumen 15*g* extending longitudinally therethrough. A guidewire lumen is defined by a guidewire tube 60*g* which extends through the lumen 15*g* inside the catheter body 11*g* and has a distal end that extends through a distal tip or cap 66*g*. The cap 66*g* has at least one irrigation outlet hole 67*g* that communicates with the lumen 15*g*. The ultrasound transmission member 16*g* extends longitudinally through the lumen 15*g* of the catheter body 11*g*, and its distal end is secured in a proximal bore of the cap 66*g*. The ultrasound transmission member 16*g* is attached adjacent its distal end to the guidewire tube 60*g*. The attachment can be accomplished by the direct use of glue, welding or fusing. Also, the attachment may be accomplished by using an attachment member 65*g*, which can be glued, welded or fused to the ultrasound transmission member 16*g* and guidewire tube 60*g*. The attachment member 65*g* can be tubular. The construction shown in FIG. 10 shows the ultrasound transmission member 16*g* attached to the guidewire tube 60*g* via the attachment member 65*g* (which can be a polymer sleeve) using any applicable glue 90*g*. The cap 66*g* and the ultrasound transmission member 16*g* may be made of the same or different materials connected together. Both these parts may also be manufactured entirely from a single piece of material without the need to separately connect each other.

FIG. 12 shows the catheter of FIG. 10 modified to include an additional radiopaque marker 100 attached to the distal portion of the guidewire tube 60*g*. If the cap 66*g* is very small or made of a polymer or a low density metal, these materials exhibit a relatively low visibility under fluoroscopy. In such a case, an additional radiopaque marker may be needed to improve visibility of the distal end 14*g* of the catheter. The radiopaque marker 100 may be placed around the guidewire tube 60g, or attached to the guidewire tube, or to the catheter body 11g (not shown), or to the ultrasound transmission member 16g (not shown), or both, using any applicable methods such as a glue or thermal fusing. The radiopaque marker 100 may also be positioned inside the distal end of the catheter body 11g (not shown) or inside the distal cap 66g (not shown). The radiopaque marker may be provided in the form of a tubular sleeve or coil (not shown). A radiopaque rod or wire (not shown) positioned inside the hole 67g may serve the same purpose as well. Such a sleeve, coil, rod or wire may be made of any radiopaque material including but not limited to platinum or gold.

FIG. 13a shows the catheter of FIG. 10 modified so that the distal end of the ultrasound transmission member 16g is attached to the guidewire tube 60g and the catheter body 11g via attachment member 65g using applicable glue 90g for further preventing or minimizing the introduction of debris into the patient's vasculature if the ultrasound transmission member 16g were to break or fracture during a medical procedure.

FIG. 13b shows the catheter of FIG. 10 modified so that the ultrasound transmission member 16g is directly attached to the guidewire tube 60g and the catheter body 11g using any applicable glue 90g, and eliminating the attachment member 65g as shown in the FIG. 13a.

FIG. 14a shows the catheter of FIG. 10 modified to include an additional radiopaque marker 101 positioned on the distal portion of the ultrasound transmission member 16g. Alternatively, the radiopaque marker 101 may be positioned freely on the ultrasound transmission member 16g and attached to the catheter body 11g using any applicable glue 120 as shown in FIG. 14b. The radiopaque marker 101 may be positioned freely or attached/affixed to the ultrasound transmission member 16g using any known technique, including but not limited to welding, soldering, fusing, glue or bonding.

FIG. 15a shows the catheter of FIG. 10 modified to include an additional radiopaque marker 1021 positioned solely on the cap 66g of the catheter 14g. Alternatively, a radiopaque marker 103 may be positioned partially on the cap 66g and partially on the catheter body 11g, as shown in FIG. 15b. The radiopaque marker 1021 may be positioned freely or attached to the cap 66g using known technique, such as welding, soldering, fusing, glue, or bonding. If the radiopaque marker 103 is partially located on the catheter body 11g and partially on the cap 66g, it can also be positioned freely or attached to one or both of these components.

FIG. 16 shows the catheter of FIG. 5 with the distal cap 66h modified to have a radial dimensional step. The same numeral designations are used in FIG. 16 to designate the same elements as in FIG. 5, except that an "h" is added to the numeral designations in FIG. 16. The distal cap 66h has two radial sections, a distal portion 110 which has a smaller dimension, and a proximal portion 112 which has a larger diameter than the portion 110. There is a transition portion 111 of the cap 66h located between the distal portion 110 and the proximal portion 112. In addition, to improve radiopacity of the cap 66h, a radiopaque marker 104 can be located around the cap 66h. The marker 104 can be located on the proximal portion 112 or on the distal portion 110 (not shown). The transition portion 111 should be smooth without any steps or edges.

FIG. 17 shows the catheter of FIG. 16 modified to provide the distal cap 66i with two radial dimensional steps. Again, the same numeral designations are used in FIG. 17 to designate the same elements as in FIG. 16, except that an "i" is added to the numeral designations in FIG. 17. The cap 66i has three dimensional sections or steps, a distal portion 120 which has the smallest dimension, an intermediate portion 122 which has a larger diameter than the distal portion 120, and a proximal portion 124 which has diameter that is larger than the distal portion 120 and the intermediate portion 122. A first transition portion 121 is located between the distal portion 120 and the intermediate portion 122, and a second transition section 123 is located between the intermediate portion 122 and the proximal portion 124. Both transition portions 121 and 123 may be configured in several different shapes or configurations, including but not limited to a rounded configuration, a flat configuration, a tapered configuration, a reverse taper configuration, or combinations thereof. Such a three-stepped configuration would further increase energy intensity (i.e., smaller area at the energy level) and improve device efficacy.

FIG. 18 illustrates a catheter that extends the principles of FIGS. 16 and 17, so the same numeral designations are used in FIG. 18 to designate the same elements as in FIGS. 16 and 17, except that a "j" is added to the numeral designations in FIG. 18. Unlike the embodiments in FIGS. 16 and 17, the distal cap 66j and the ultrasound transmission member 16j are made of the same piece of material, so there is no separate attachment between them. This can be accomplished by machining laser cut, deposition or other forming methods. The distal cap 66j has two different radial dimensions, a distal portion 130 and a proximal portion 132 that has a greater diameter than the distal portion 130. The distal portion 130 has a longitudinally tapered configuration, while the proximal portion 132 has a continuous longitudinal configuration. A concave transition 133 is provided between the distal portion 130 and the proximal portion 132. Such a transition 133 may further increase the ultrasound catheter efficacy because of the additional mechanical cutting edge 131 provided by this configuration.

FIG. 19 illustrates modifications made to the catheter in FIG. 10 where the distal cap 66k is provided with a radial dimensional step having a different configuration to that in FIG. 10. Therefore, the same numeral designations are used in FIG. 19 to designate the same elements as in FIG. 10, except that a "k" is added to the numeral designations in FIG. 19. The distal cap 66k has two different radial dimensional sections, with a distal portion 140 and a proximal portion 142 separated by a transition portion 141. By reducing the size of the distal cap 66k adjacent its distal-most portions (where the catheter would contact a target tissue), the intensity of the ultrasound energy will be increased, thereby improving the ablation capabilities of the ultrasound catheter 10k. The catheter 10k is capable of operating with a conventional guidewire 25k. The guidewire 25k can be positioned within the guidewire lumen 60k positioned within the catheter body 11k, and attached to the distal cap 66k via any suitable medical grade glue 150. The catheter 10k can be used to ablate any unwanted material in a blood vessel or conduit in the human body. As an example, in FIG. 19, the distal end 14k of the catheter 10k is positioned against an obstruction 200 (e.g., vascular abstraction or atherosclerotic plaque) located in a vessel 201. The distal portion 140 of the cap 66k, while positioned against the obstruction 200 and activated, will create a small pilot entry lumen 203 that further enhances the ablation process because of the higher energy intensity. Once this pilot lumen 203 has been created, the ablation process caused by the larger proximal portion 142 of the cap 66k will continue. The length of the distal-most cross sectional area with the smallest diameter depends on the overall size of the catheter 10k. For endovascular applications, the diameter of the cap 66k varies between 0.2 mm to 6 mm, the length of the distal portion 140 is preferably between 0.1 mm and 5 mm, and preferably about 0.5 mm. A cap 140 with such a short distal portion 140 will be less prone to unwanted perforation because of the protective effect afforded by the larger-diameter portion 142 of the cap 66k being located nearby. Without the smaller distal portion 140, the distal end 14k of the catheter 10k would otherwise be much larger and the energy intensity would be lower, thereby making it difficult to initiate the ablation process, or causing the start of the ablation process to take more time.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. An ultrasound catheter comprising:
   an elongate flexible catheter body having a proximal end, a distal end and at least one lumen extending longitudinally therethrough;
   an ultrasound transmission member extending longitudinally through the lumen of the catheter body, the ultrasound transmission member having a proximal end that is coupled to a separate ultrasound generating device;
   a tip coupled to the distal end of the ultrasound transmission member, wherein the tip has at least one radial dimensional step having a contact surface facing away from the ultrasound transmission member and in a distal direction, wherein a cross-sectional area of the tip at a location on a distal side of the contact surface is less than a cross-sectional area of the tip at the contact surface; and
   an intermediate member attached to the catheter body and having a contact surface facing at least a portion of the contact surface on the tip and in a proximal direction, the contact surface of the intermediate member being configured to contact the contact surface of the tip so as to prevent the tip from becoming dislodged from the catheter body, wherein a cross-sectional area of the intermediate member at a location on a proximal side of the contact surface of the intermediate member is less than a cross-sectional area of the intermediate member at the contact surface of the intermediate member.

2. The catheter of claim 1, wherein the tip and the ultrasound transmission member are made of the same piece of material.

3. The catheter of claim 1, wherein the tip further comprises a guidewire aperture.

4. The catheter of claim 3, wherein a guidewire tube is attached to a guidewire aperture inside the tip.

5. The catheter of claim 1, wherein the dimensional step separates the tip into two sections separated by a transition, a first section having a first radial dimension and a second section having a second different radial dimension.

6. The catheter of claim 5, wherein the transition between the first section and the second section has one of the following configurations: flat, rounded, tapered, concave or any combination.

7. The catheter of claim 5, wherein the first section has a continuous longitudinal diameter.

8. The catheter of claim 5, wherein the first section has a tapered configuration.

9. The catheter of claim 5, wherein the second section has a continuous longitudinal diameter.

10. The catheter of claim 5, wherein the second section has a tapered configuration.

11. The catheter of claim 1, wherein the tip has two or more dimensional steps.

12. The catheter of claim 1, wherein a proximal section of the catheter body has a diameter that is greater than a diameter of a distal section of the catheter body.

13. The catheter of claim 12, wherein the intermediate member has an outer diameter which substantially matches the diameter of the distal section of the catheter body.

14. The catheter of claim 1 further comprising an irrigation outlet, the irrigation outlet being disposed on a proximal side of the intermediate member.

15. The catheter of claim 14, wherein the ultrasound transmission member is coaxially disposed with the catheter body.

16. The catheter of claim 1, wherein the catheter further comprises a cap coupled to the tip.

17. The catheter of claim 16, wherein the cap has at least one radial dimensional step.

18. An ultrasound catheter comprising:
    an elongate body having a proximal end, a distal end and at least one lumen extending longitudinally therethrough;
    an ultrasound transmission member extending through the lumen and having a proximal end and a distal end, the proximal end being configured to couple to a separate ultrasound generating device;
    a flared tip coupled to the distal end of the ultrasound transmission member, at least a portion of the tip having a maximum diameter that is greater than a diameter of the ultrasound transmission member; and
    an intermediate member having a proximal end and a distal end, the intermediate member being attached to the body and surrounding at least the portion of the tip having the maximum diameter, the proximal and distal ends of the intermediate member each having an inner diameter that is less than the maximum diameter of the tip.

19. The catheter of claim 18, wherein the tip has at least one radial dimensional step, and wherein the intermediate member is seated on the at least one radial dimensional step.

20. An ultrasound catheter comprising:
    an elongate body having a proximal end, a distal end and at least one lumen extending longitudinally therethrough;
    an ultrasound transmission member extending through the lumen and having a proximal end and a distal end, the proximal end being configured to couple to a separate ultrasound generating device;
    a tip coupled to the distal end of the ultrasound transmission member and having a maximum diameter;
    a cap coupled to the tip by an attachment structure, the cap and the tip at least partially defining a groove therebetween; and
    an intermediate member attached to the body and having a proximal end and a distal end, at least a portion of the intermediate member being disposed within the groove, wherein the proximal and distal ends of the intermediate member each have an inner diameter that is less than the maximum diameter of the tip.

21. The catheter of claim 20, wherein the attachment structure comprises glue.

22. The catheter of claim 20, wherein the attachment structure is a weld.

23. The catheter of claim 20, wherein the attachment structure is a fuse weld.

* * * * *